United States Patent [19]

Koivisto

[11] Patent Number: 5,528,645
[45] Date of Patent: Jun. 18, 1996

[54] METHOD AND DEVICE FOR THE ADJUSTMENT OF IMAGING VALUES IN A PANORAMIC X-RAY IMAGING APPARATUS

[75] Inventor: Juha Koivisto, Helsinki, Finland

[73] Assignee: Instrumentarium Corp., Finland

[21] Appl. No.: 498,803

[22] Filed: Jul. 6, 1995

[30] Foreign Application Priority Data

Jul. 18, 1994 [FI] Finland ................................. 943404

[51] Int. Cl.⁶ ..................................................... H05G 1/64
[52] U.S. Cl. .......................... 378/37; 378/98.7; 378/98.8
[58] Field of Search ................................. 378/38, 39, 96, 378/98.6, 98.7, 98.8

[56] References Cited

U.S. PATENT DOCUMENTS

| | | | |
|---|---|---|---|
| 5,142,557 | 8/1992 | Toker et al. | 378/37 |
| 5,315,631 | 5/1994 | Hillen et al. | 378/98.8 |
| 5,461,658 | 10/1995 | Joosten | 378/98.7 |

FOREIGN PATENT DOCUMENTS

92/22188 12/1992 WIPO.

OTHER PUBLICATIONS

Charge–coupled device detector: Performance considerations and potential for small–field mammographic imaging applications—Med. Phys., vol. 19, No. 4, Jul./Aug. 1992, pp. 1015–1023, Karellas et al.

*Primary Examiner*—Don Wong
*Attorney, Agent, or Firm*—Andrus, Sceales, Starke & Sawall

[57] ABSTRACT

The invention relates to a method and an apparatus for the adjustment of imaging values in a panoramic x-ray imaging apparatus. The imaging device comprises a CCD detector which is manipulated in such a manner that the domains to be imaged in an examined object are the first to fall in line with a serial register included in the edge of the CCD detector. The measuring information received from the serial register is used as preliminary information about an intensity received on the image field and this information is used as a basis for the adjustment of imaging values for optimizing the signal-to-noise ratio of the CCD detector.

5 Claims, 2 Drawing Sheets

METHOD AND DEVICE FOR THE ADJUSTMENT OF IMAGING VALUES IN A PANORAMIC X-RAY IMAGING APPARATUS

The present invention relates to a method for the adjustment of imaging values in a panoramic x-ray imaging apparatus, said method comprising such a manipulation of a CCD detector serving as an imaging device that the domains to be imaged in an examined object fall first in line with a serial register included in the edge of the CCD detector.

The invention relates also to a panoramic x-ray imaging apparatus, wherein the imaging device comprises a CCD detector which is manipulated in such a manner that the domains to be imaged in an examined object fall first in line with a serial register included in the edge of the CCD detector.

In the panoramic x-ray equipment constructed with a CCD element (CCD=Charge Coupled Device), exactly the same way as in the equipment recording on film, the correct adjustment of exposure is of paramount importance for creating a correct contrast and brightness for the image.

In the x-ray equipment based on the indirect detection of quanta carried out by a CCD detector, the number of shades of gray depends on the dynamics of the detector and amplifier electronics as well as on the x-ray quantum photoelectron conversion ratio produced by a scintillator layer and optics. If the exposure is not adjusted properly, the CCD experiences in the overexposure situation in its picture elements (pixels) an overflow of charge to adjacent pixels and, thus, the image "darkens" over this section and the spatial resolution decreases. In the underexposure situation, on the other hand, the CCD is not capable of producing the best possible signal/noise ratio. (In reality, S/N is dependent on the square root of a signal). Thus, the number of detectable shades of gray decreases and the image quality deteriorates.

A conventional odontological x-ray diagnostical apparatus includes a rotatable unit, mounted on a vertical shaft and having a supporting frame with one end carrying an x-ray source and the other being provided with a secondary slot, the speed of a film located therebehind being synchronized with imaging motion.

In an apparatus of this invention, the film is replaced with a scintillation material as well as a CCD detector provided with a fiberoptical reducer. The scintillation material converts the energy of x-ray quanta to light, which in turn produces on the CCD surface a charge corresponding to the intensity. The charge is converted to voltage by means of an amplifier. The fiberoptical reducer, on the other hand, can be used for increasing the size of an area to be imaged at the expense of resolution.

An object of the invention is to provide a method and apparatus for effecting the automatic exposure in an odontological or other x-ray diagnostical apparatus based on the manipulation of a CCD in such a manner that, regardless of the thickness or density of a tissue layer, it is possible to prevent the overexposure as well as to adjust the exposure optimally in view of the CCD for an improved brightness and contrast.

A particular object of the invention is to provide a method and apparatus capable of optimizing the current, voltage and exposure time values needed in exposure and, at the same time, of minimizing the radiation dose received by a person being examined.

These objects are achieved on the basis of the characterizing features set forth in the annexed claims.

The invention will now be described in more detail with reference made to the accompanying drawings, in which FIG. 1 shows the principle of a CCD panoramic x-ray imaging apparatus. For the sake of simplicity, the figure does not include a fiberoptical reducer preceding the CCD and coated with a scintillation material;

Figure 3A:
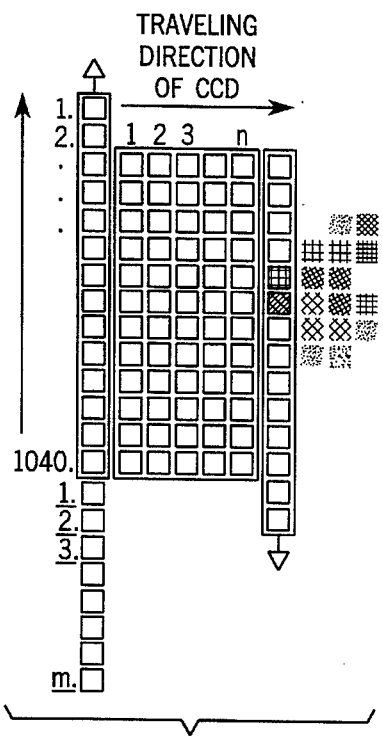
Figure 4:
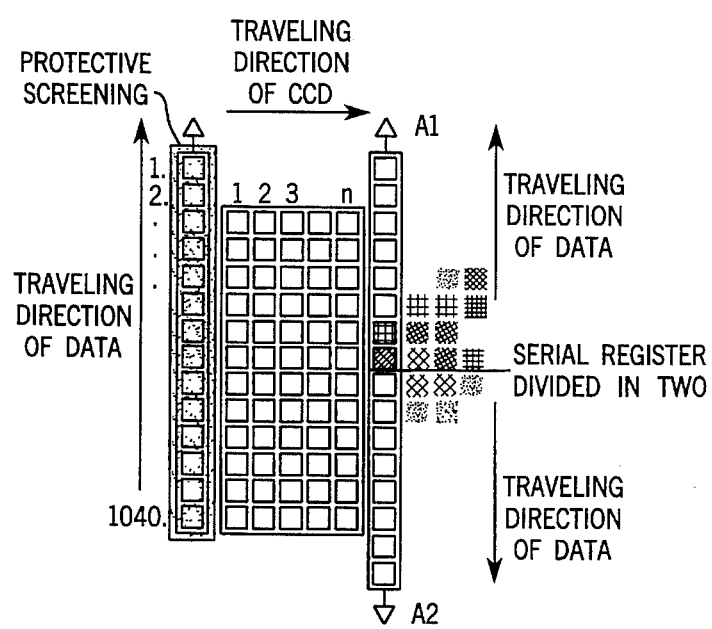

FIGS. 3a, b and c illustrate the step-by-step movement of a CCD across an object being examined;

FIG. 4 shows a CCD detector with an equally divided serial register.

Image production with a panoramic x-ray apparatus

Figure 1:
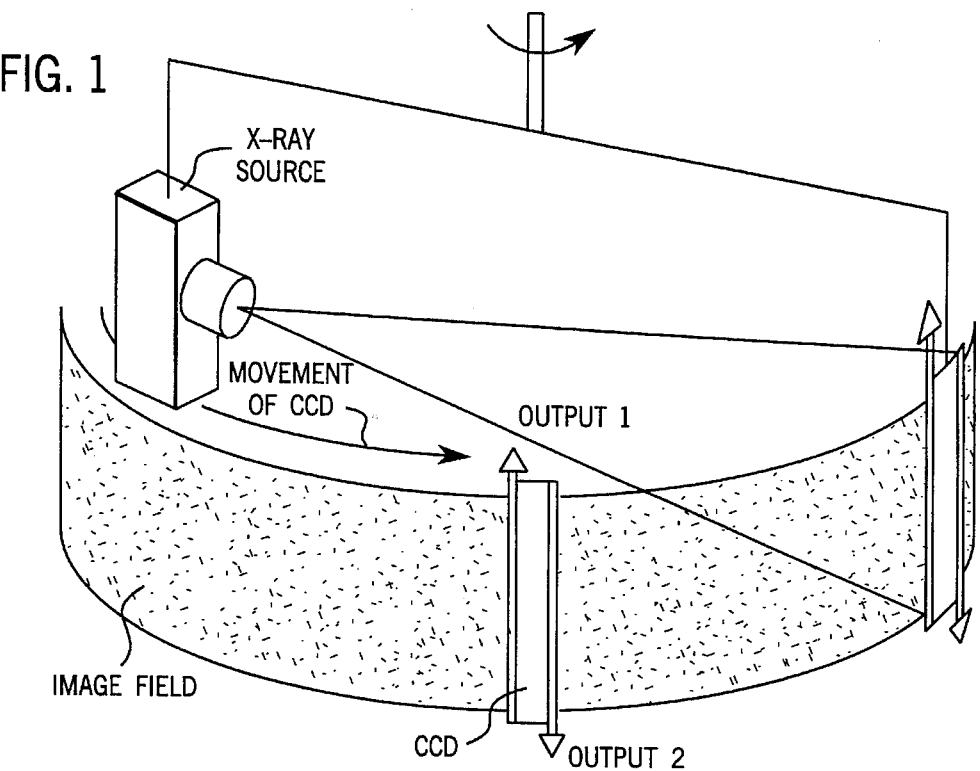
Figure 2A:
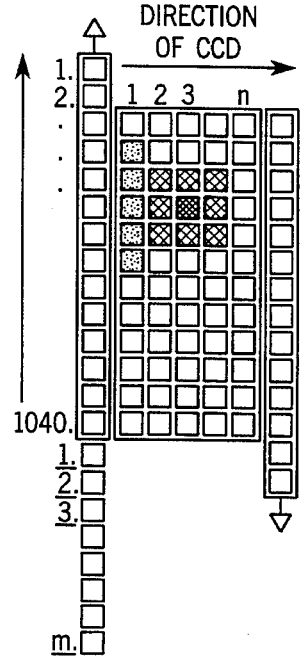
FIG. 2a shows the exposure of a CCD image area.
Figure 2B:
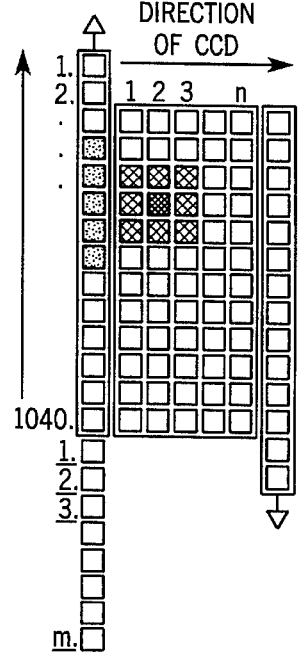
FIG. 2b shows a line transfer from the image area to a serial register.

As a working hypothesis for better understanding of the matter, it can be envisaged that, during the course of imaging, the movement of an x-ray source is synchronized with the line transfers of a CCD as follows: During each exposure, both the source and the detector remain stationary for a time t, whereby a charge corresponding to the intensity is generated in the CCD (see FIG. 2a, a type of rastering correlates to a type of intensity). After each exposure, the CCD and the x-ray source supporting frame are rotated over a distance equalling the distance between two pixel lines (for example 50 µm). During the exposure, a charge generated in the CCD is transferred in a corresponding manner counter to the movement advancing direction in such a way that line 1 transfers to a serial register (see FIG. 2b), line 2 to the previous location of line 1 etc. In such a procedure, the exposure of an object fallen over pixel line 2 can be continued in the location of pixel line 1, the exposure of an object fallen over pixel line 3 can be continued in the location of line 2 etc.

Figure 2C:
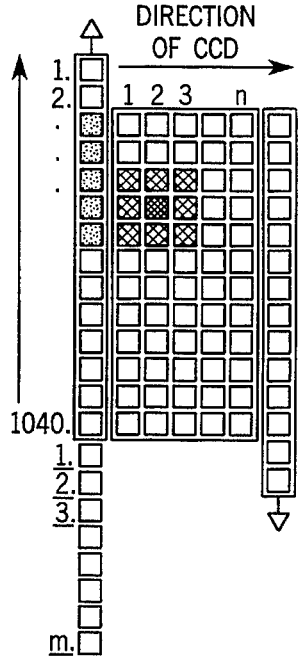
FIG. 2c shows a transfer of charges effected in the serial register.

The output of information included in a line clocked into the serial register is effected by shifting the pixels of a CCD upwards in the direction of an output amplifier (see FIG. 2c), whereby the charge of pixel 1 transfers into the output amplifier, the charge of pixel 2 transfers to the location of pixel 1 etc.

Performing an automatic exposure

The principle of an automatic exposure of this invention is as follows.

The x-ray source and the CCD are shifted towards a serial register which is first in the CCD traveling direction in such a manner that the object falls in line with the serial register (see FIG. 3a). This procedure provides advance information about the imminent intensity of an image field which can be used as a basis for calculating each exposure time per line.

The pixels of an image field are attempted to be exposed in such a manner that the charge of a pixel after the transfers across the image field corresponds to the maximum acceptable charge per pixel. Tabulation of the exposure times per line is carried out concurrently.

An automatic exposure according to the method can be carried out as follows: The CCD elements are usually provided with two serial registers, one along each side of an image field at the opposite edges, for transferring the image-field information therein for a readout. The charge of a CCD, which is conventionally held stationary throughout the imaging session, is read either from one or from both serial registers. In a system according to this method, the CCD and the x-ray generator are shifted in such a manner that the charge of an image field is read out of the serial register which is last (located at the trailing edge) relative to the CCD traveling direction. (Imaging can also be carried in such a manner that the CCD and the x-ray source are manipulated in both directions). When imaging is effected as described above, the serial register which is first in the CCD traveling direction reaches the area subjected to examination. (The serial register, which is photosensitive the same way as the image field of a CCD, is approximately fourfold in its charge retaining capacity when compared to a normal picture element, a pixel). Upon the arrival of a CCD in the area to be imaged, the serial register area is allowed to expose for a predetermined time $t_{int}$ (e.g. $t_{int}$ =10 mS), whereafter the charge is clocked from the serial register to an output amplifier. Information obtained from the amplifier is registered digitally. An attempt is made to select the first exposure time so as not to produce a charge overflow in the pixels of the serial register.

A charge produced in the exposure of a serial register is used as a basis for computing the optimal exposure time for example as follows:

Presuming that

The CCD image field includes 10 lines of pixels in the direction of motion serial registers on either side of the image field each pixel of the image field "accommodates" $Q_{max}$ =10$^6$ electrons a pixel in the serial register accommodates 4×10$^6$ electrons.

On the basis of what is stated above, it can be computed that, if a CCD stops at each line for an equal time to effect exposure, the duration of a single stop must be such that the maximum number of electrons corresponding to a single exposure is 10$^6$/ 10 lines=10$^5$ electrons. If the maximum charge produced in any pixel of a serial register within the 10 mS exposure time is for example $Q_{ref}$=80,000, the optimum exposure time $t_{opt1}$ can be computed as $t_{opt1}$=10 mS×10$^5$ e$^-$/80,000 e$^-$=12,5 mS. When this exposure time used at the first line of an image field after the CCD shift, the maximum value obtained at a single pixel will be 100,000 e$^-$. Concurrently with the line of pixels in the image field, the exposure is effected the same way and for an equal time on a new object located on top of the serial register. The charge is clocked to the output after the exposure exactly the same way as in the first time. In various exposure conditions, depending on the power of intensity received in the serial register, the procedure will be as follows.

1) If none of the charges included in the pixels of a serial register does not exceed the maximum acceptable charge (10$^5$ electrons), the same exposure time $t_{opt1}$ is used for the exposure of the next line as well (since the maximum intensity of an image field determines the maximum exposure time). According to the initial hypothesis, the CCD includes 10 lines of pixels (R1–R10) in the traveling direction of movement and, thus, if none of the subsequent nine lines (R2–R1) entering the serial register thereafter displays the exceeding of a maximum acceptable charge, the resulting total exposure time will be $t_{tot}$=10×$t_{opt1}$. Since the local point of maximum intensity included in an image field is clocked in the serial register, the highest value found either in the image field or in the serial register can be used for computing a new exposure time.

2) If any of the values of a line having entered the serial register during the next exposure exceeds the highest acceptable value, the obtained maximum value will be used for computing a new exposure time $t_{opt2}$. The total exposure time of each line, which is the sum of partial exposure times, will be recorded in a line-related table.

After the exposure of an image area, the exposure time information included in the table can be used for standardizing the intensity information of each line to match each other. For example, in an odontological apparatus the standardization can be performed on the basis of an intensity received from the area of some special location, such as a maxilla.

A method of the invention provides an advantage over the conventional CCD-effected exposure as follows: The signal-to-noise ratio (S/N) is on high signal levels dependent on a statistical noise $N_{shot}$ which is≈√S. On low signals, on the other hand, the S/N ratio is restricted by a noise $N_{dark}$ caused by a dark current and enveloped in the pixels of a CCD as well as by a read noise $N_{read}$. The total noise can be calculated from the expression:

$$N_{tot} = \sqrt{N_{Read}^2 + N_{Shot}^2 + N_{Dark}^2}$$

The effect of adjusting an exposure time on the S/N ratio is specified by means of the following example: The picture element of a conventional CCD circuit has a charge retaining capacity of 10$^6$ electrons, a dark current of about 200 e$^-$/pixel/s. At high reading frequencies, the amplifier electronics has typically a read noise of about 100 e$^-$. The following table shows calculations of signal-to-noise ratios at various exposure time values. As shown in the table, the S/N on a high signal is proportional to the square root of a signal, If the signal is 10% of a maximum acceptable signal, the corresponding S/N will be 316. However, the signal-to-noise ratio can be improved by extending the exposure time from 10 mS to 100 milliseconds (see line 2) for improving the S/N from 316 to 999.75. Accordingly, the table can be used to verify that the signal-to-noise ratio improves when progressing towards lower signal values. In practice, the improved signal-to-noise ratio is beneficial by increasing the resolution at the bottom part (toe) of a logarithmic curve corresponding to the exposure of film, in which part the optical density is below 0.5. The adjustment of exposure in accordance with this invention also expands an available exposure area as it can be used for detecting intensity variations which would otherwise be covered by noise (see line 5). The example employs the variation of exposure time by factor 10 but, according to the situation, the extension of exposure time is also possible by some other factor, whereby a higher exposure-time variation factor improves the S/N ratio even further.

|    | Tint         | S(e−)                  | $N_{dark}$      | S/N           |
|----|--------------|------------------------|-----------------|---------------|
| 1  | 10 mS        | 10$^6$                 | 2e−             | 999.95        |
| 2. | 10 mS → 100 mS | 10$^5$ → 10$^6$      | 2e− → 20e−      | 316 → 999.75  |
| 3. | 10 mS → 100 mS | 10$^3$ → 10$^4$      | 2e− → 20e−      | 30 → 97.6     |
| 4. | 10 mS → 100 mS | 10$^2$ → 10$^3$      | 2e− → 20e−      | 7 → 25.8      |
| 5. | 10 mS → 100 mS | 10$^1$ → 10$^2$      | 2e− → 20e−      | 0.9 → 4.1     |

The above working hypothesis for facilitating the examination presumes that the CCD detector detecting x-ray quanta is stopped in the alignment with each line for the duration of measuring. However, since the source carried at the end of a rotary frame as well as the detector are practically impossible to stop for exposure in a short time because of the system moment of inertia (and other such factors), the invention must be practiced while the x-ray source and the CCD are in continuous motion.

According to the basic concept of the invention, automatic exposure is accomplished in such a manner that the serial register which is first in the traveling direction of a moving CCD element is first to reach a target to be imaged and, thus, the quanta falling thereon provide preliminary information about the exposure falling on the image area. If the movement of the CCD could be stopped at each pixel for the duration of exposure and the data transferred away from the serial register prior to a new exposure, a charge would be vertically summed up in the pixels of the serial register (phantom figure). The strength of this charge depends on a relationship between the exposure time and the serial register reading time. In other words, if the exposure time is long relative to the serial register reading time, there is just a minor error occurred in the evaluation of an exposure time.

If the CCD moves during the course of exposure (which is a necessary requirement in view of exploiting the invention), the error resulting in the evaluation of exposure can be computed by means of the following example.

Figure 3B:
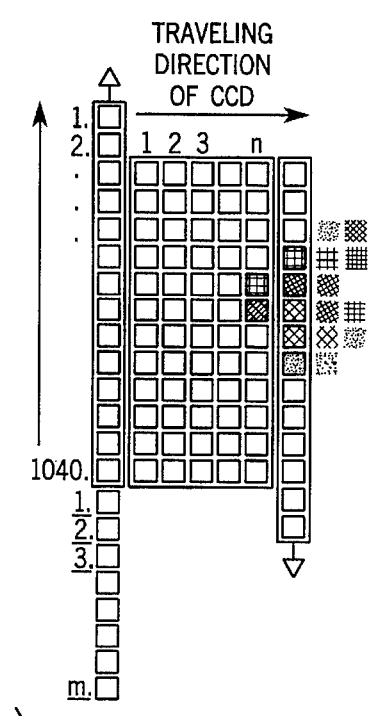
Figure 3C:
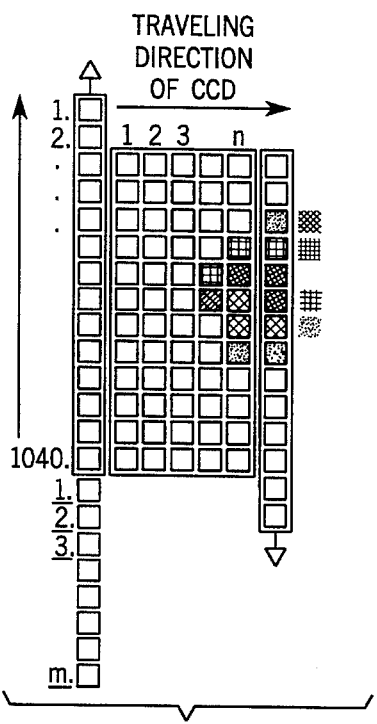

The detection of quanta is effected by using a detector as shown in FIG. 4. This detector is similar to the one shown in FIGS. 2 and 3. FIG. 4 is completed by including components already existing in the CCD and useful in a method of the invention.

In a conventional panoramic x-ray apparatus, both the source and the imaging head have a speed of movement varying within the range of 5–32 mm/s depending on the exposure situation. When the method is carried out with a standard type CCD (EEV15,17 μm pixels), the reducer (2:1) and the scintillator have a pixel size of 54 μm×54 μm effective for a CCD. With the maximum imaging head movement, the resulting pixel frequency will be (32 mm/s) /54 μm=592 pixels/s, whereby the crossing of a single line of pixels takes 1,68 mS. At a slower speed, respectively, the resulting values will be 93 pixels/s and 10,8 mS.

Usually, the serial register of a CCD element is divided in two (see FIG. 4) in such a manner that a charge of the bottom half (512 pixels) is shifted in the direction of an amplifier A2 and a charge of the top half (512 pixels) is transferred to an amplifier A1. (Naturally, the charge can be delivered by way of just either one of the amplifiers). The transfer of a charge into various serial registers is effected by means of a three-phase clock pulse having a maximum frequency of about 1–10 MHz. As the clocking of a serial register is effected by using the frequency of 1 MHz, the clocking out of one half of the serial register takes 512 μS and, respectively, 51,2 μS at the clock frequency of 10 MHz. When the clocking of a serial register is carried out during the course of exposure (and movement), there will be some build-up of a phantom image the same way as when the CCD remains stationary. The phantom image, i.e. an error made by the exposure automatics, can be calculated on the basis of a movement in the traveling direction of the CCD and the clocking rate of a serial register.The following table discloses times spent for the exposure and transfer of a line as well as corresponding percentages.

| Speed of CCD | Crossing a line | Exposure/ transfer time | %/%– proportions |
|---|---|---|---|
| CCD clocking frequency 1 MHz | | | |
| 32 mm/S | 1.68 mS | 1.1755 mS/512 μS | 70/30 |
| 5 mm/S | 10.8 mS | 10.28 mS/512 μS | 95.3/4.7 |
| CCD clocking frequency 10 MHz | | | |
| 32 mm/S | 1.68 mS | 1.62 mS/51.2 μS | 97/3 |
| 5 mm/S | 10.8 mS | 10.7488 mS/51.2 μS | 99.5/0.5% |

It can be concluded on the basis of the table that by using a high serial register clocking frequency it is possible to apply a method of the invention intended for automatic exposure also as required by the exposure effected during the course of continuous motion.

Neither does the continuous motion of an x-ray source and a CCD cause problems in the actual build-up of an image, since the transfer of a charge from the image area towards the output serial register is effected in such a manner that the mechanical movement of a CCD and the average of a charge transfer speed match each other.

I claim:

1. A method for the adjustment of imaging values in a panoramic x-ray imaging apparatus, said method comprising such a manipulation of a CCD detector serving as an imaging device that the domains to be imaged in an examined object fall first in line with a serial register included in the edge of the CCD detector, characterized in that the exposure value of the serial register is used as preliminary information about an intensity received on the image field and this information is used as a basis for the adjustment of imaging values.

2. A method as set forth in claim 1, characterized in that the measuring information received from the serial register is used for the adjustment of imaging values by optimizing the signal-to-noise ratio of the CCD detector.

3. A method as set forth in claim 1, characterized in that areas in the imaging information essential in terms of the adjustment are identified prior to the build-up of an image on the imaging device.

4. A panoramic x-ray imaging apparatus, wherein the imaging device comprises a CCD detector which is manipulated in such a manner that the domains to be imaged in an examined object fall first in line with a serial register included in the edge of the CCD detector, characterized in that the measuring information received from the serial register is used for the adjustment of imaging values before the area to be imaged arrives in an image area subjected to the adjustment.

5. An apparatus as set forth in claim 4, characterized in that the x-ray source and the CCD detector are in continuous motion also during the actual build-up of an image while the transfer of a charge from the image area towards the output serial register is effected in such a manner that the mechanical traveling speed of the CCD detector and the average of a charge transfer speed essentially match each other.

* * * * *